(12) United States Patent
Keller (10) Patent No.: US 7,963,042 B2
(45) Date of Patent: Jun. 21, 2011

(54) MICRO SURGICAL CUTTING INSTRUMENTS

(75) Inventor: Christopher Guild Keller, El Cerrito, CA (US)

(73) Assignee: MynoSys Cellular Devices, Inc., Albany, CA (US)

( * ) Notice: Subject to any disclaimer, the term of this patent is extended or adjusted under 35 U.S.C. 154(b) by 410 days.

(21) Appl. No.: 12/123,240

(22) Filed: May 19, 2008

(65) Prior Publication Data

US 2009/0131961 A1     May 21, 2009

Related U.S. Application Data

(63) Continuation of application No. PCT/US2006/061459, filed on Dec. 1, 2006.

(60) Provisional application No. 60/741,200, filed on Dec. 1, 2005.

(51) Int. Cl.
*B26B 9/00* (2006.01)
*B26B 9/02* (2006.01)

(52) U.S. Cl. .......................................... 30/350; 30/357

(58) Field of Classification Search ............ 30/349, 30/350, 346.54, 346.55, 357; 606/167, 170, 606/172; 76/104.1, DIG. 8, DIG. 9
See application file for complete search history.

(56) References Cited

U.S. PATENT DOCUMENTS

| | | | | |
|---|---|---|---|---|
| 1,814,182 A | * | 7/1931 | Parker | 30/349 |
| 1,814,959 A | * | 7/1931 | Parker | 30/349 |
| 2,319,607 A | * | 5/1943 | Kevorkian et al. | 30/357 |
| 2,408,790 A | * | 10/1946 | Mack | 76/104.1 |
| 3,160,967 A | * | 12/1964 | Nichols | 30/349 |
| 3,387,368 A | * | 6/1968 | Scheck | 30/350 |
| 3,681,846 A | | 8/1972 | Gerber | |
| 3,761,374 A | * | 9/1973 | Bromer et al. | 30/346.55 |
| 3,911,579 A | * | 10/1975 | Lane et al. | 30/346.54 |
| 3,986,260 A | * | 10/1976 | Whiteford | 30/349 |
| 4,534,827 A | * | 8/1985 | Henderson | 30/346 |
| 4,640,169 A | * | 2/1987 | Fromson et al. | 30/350 |
| 4,896,424 A | * | 1/1990 | Walker | 76/104.1 |
| 4,991,481 A | * | 2/1991 | Gerber | 30/357 |
| 5,018,347 A | * | 5/1991 | Feilen | 30/349 |
| 5,221,415 A | | 6/1993 | Albrecht et al. | |
| 5,232,568 A | | 8/1993 | Parent et al. | |
| 5,312,643 A | | 5/1994 | Yamamoto et al. | |
| 5,317,938 A | | 6/1994 | de Juan, Jr. et al. | |
| 5,399,232 A | | 3/1995 | Albrecht et al. | |
| 5,437,656 A | * | 8/1995 | Shikani et al. | 604/891.1 |
| 5,569,292 A | | 10/1996 | Scwemberger et al. | |
| 5,579,583 A | | 12/1996 | Mehregany et al. | |
| 5,669,144 A | * | 9/1997 | Hahn et al. | 30/346.54 |
| 5,728,089 A | | 3/1998 | Lal et al. | |

(Continued)

FOREIGN PATENT DOCUMENTS

WO    WO 9639937 A1 * 12/1996

(Continued)

OTHER PUBLICATIONS

Vangbo et.al., "Precise Mask Alignment to the Crystallographic Orientation of Silicon Wafers Using Wet Anisotropic Etching," *J. Micromech. Microeng.*, vol. 6, pp. 279-294, 1996.

(Continued)

*Primary Examiner* — Jason Daniel Prone
(74) *Attorney, Agent, or Firm* — Levine Bagade Han LLP (57) ABSTRACT

The present invention relates to methods and apparatus for micro surgical blades, knives and assemblies.

33 Claims, 8 Drawing Sheets

U.S. PATENT DOCUMENTS

| | | | |
|---|---|---|---|
| 5,792,137 | A | 8/1998 | Carr et al. |
| 5,795,648 | A * | 8/1998 | Goel et al. ............... 30/346.55 |
| 5,842,387 | A | 12/1998 | Marcus et al. |
| 5,928,161 | A | 7/1999 | Krulevitch et al. |
| 5,980,518 | A | 11/1999 | Carr et al. |
| 5,994,160 | A | 11/1999 | Niedermann et al. |
| 6,075,683 | A * | 6/2000 | Harwood et al. ............ 360/135 |
| 6,105,261 | A * | 8/2000 | Ecer ............................. 76/104.1 |
| 6,106,751 | A * | 8/2000 | Talbot et al. .................... 264/81 |
| 6,260,280 | B1 * | 7/2001 | Rapisardi ....................... 30/357 |
| 6,263,581 | B1 * | 7/2001 | Forte .............................. 30/349 |
| 6,319,474 | B1 * | 11/2001 | Krulevitch et al. ............ 30/278 |
| 6,330,750 | B1 * | 12/2001 | Meckel ........................... 30/350 |
| 6,375,148 | B1 * | 4/2002 | Talbot et al. .................. 249/105 |
| 6,389,699 | B1 * | 5/2002 | Ecer ........................... 30/346.54 |
| 6,615,496 | B1 * | 9/2003 | Fleming et al. ................ 30/350 |
| 6,706,203 | B2 | 3/2004 | Barth et al. |
| 7,059,054 | B2 * | 6/2006 | Pilchowski .................... 30/350 |
| 7,396,484 | B2 * | 7/2008 | Daskal et al. ................. 216/101 |
| 2002/0078576 | A1 | 6/2002 | Carr et al. |
| 2002/0142182 | A1 * | 10/2002 | Peker et al. .................... 30/350 |
| 2003/0208911 | A1 | 11/2003 | Fleming et al. |
| 2005/0132581 | A1 * | 6/2005 | Jessing ........................ 76/104.1 |
| 2005/0144789 | A1 * | 7/2005 | Pilchowski .................... 30/350 |
| 2005/0210684 | A1 * | 9/2005 | Newman ........................ 30/350 |
| 2007/0056404 | A1 * | 3/2007 | Pricone ......................... 76/25.1 |
| 2007/0157475 | A1 * | 7/2007 | King et al. ................ 30/346.54 |
| 2007/0275179 | A1 * | 11/2007 | strand et al. ................... 30/350 |
| 2009/0048537 | A1 * | 2/2009 | Lydon et al. .................. 600/585 |
| 2009/0099534 | A1 * | 4/2009 | Lee et al. ...................... 604/272 |
| 2009/0177217 | A1 * | 7/2009 | Keller ........................... 606/167 |
| 2010/0024222 | A1 * | 2/2010 | Akari et al. ............... 30/346.54 |
| 2010/0234864 | A1 * | 9/2010 | Keller ........................... 606/159 |

FOREIGN PATENT DOCUMENTS

| | | |
|---|---|---|
| WO | WO 9947341 A1 * | 9/1999 |
| WO | WO 2005/037070 | 4/2005 |
| WO | WO 2007070745 A2 * | 6/2007 |
| WO | WO 2007092852 A2 * | 8/2007 |

OTHER PUBLICATIONS

PCT International Patent Application No. PCT/US2006/061459 filed Dec. 1, 2006 in the name of Keller, International Search Report and Written Opinion mailed Oct. 2, 2007.

PCT International Patent Application No. PCT/US2007/061701 filed Feb. 6, 2007 in the name of Keller, International Search Report and Written Opinion mailed Sep. 11, 2008.

* cited by examiner

PRIOR ART

MICRO SURGICAL CUTTING INSTRUMENTS

This application is a continuation of International Application No. PCT/US2006/061459 filed Dec. 1, 2006 which is a non-provisional of U.S. Provisional Application No. 60/741,200 entitled Micro Surgical Cutting Instruments, filed on Dec. 1, 2005, the entirety of which are incorporated by reference herein.

FIELD OF THE INVENTION

The present invention relates to methods and apparatus for micro surgical blades, knives and assemblies.

BACKGROUND OF THE INVENTION

Conventional metal, diamond tipped or other similar type knives have blade edges or cutting surfaces that are considerably large when viewed on an atomic scale. Typically such knives have cutting edges ranging from 500 angstroms to about 1000 angstroms. Typically, such knives provide poor surgical precision and cause unnecessary destruction of tissue when viewed at the cellular level.

Presently, atomic force microscopy uses devices having atomically sharp-tips for the manipulation and separation of cells. Such devices and methods are found in U.S. Pat. Nos. 5,221,415; 5,399,232; and 5,994,160 the entirety of each of which are incorporated by reference herein. Additional information regarding devices used in atomic force microscopy may be found in Journal of Nanoscience and Nanotechnology 2002, V 2, No. 1, pp 55-59, and Journal of Microelectromechanical Systems V 6, No. 4, December 1997, pp. 303-306 the entirety of which are also both incorporated by reference herein.

References describing the fabrication of micro knives from single crystal silicon include U.S. Pat. Nos. 5,728,089; 5,317, 938; 5,579,583; 5,792,137; 5,842,387; 5,928,161; 5,944,717; 5,980,518; 6,319,474; 6,615,496; 6,706,203; and U.S. patent application Nos. 200210078576; 200310208911; 200510132581; and 200510144789 the entirety of each of which is incorporated by reference herein. Most conventional micro-knives rely on silicon as the cutting blade. Problems may be encountered as silicon is too soft to provide a satisfactory cutting surface. As a result, silicon tends to dull quickly. Moreover, silicon is not transparent to visible light so it is not suitable for applications where it is desirable to see through the blade for precise alignment to the object to be cut.

Accordingly, there remains a need for an improved micro-surgical cutting instrument.

SUMMARY OF THE INVENTION

The devices and method described herein teach micromachined blades, knives and cutting instruments. Such micro-machined devices are atomically sharp as described below. Such a construction provides precise cutting of tissue while minimizing collateral damage to tissues.

In typical applications, a micro-machined blade or micro-knife undergoes an application of a small force. Such a force may be the amount of force necessary to separate cells (e.g., less than 10 millinewtons). Therefore when cutting tissue with a micro-knife, the drag force applied to the knife must be minimized. In those devices used to cut a single cell in a petri dish there is no significant, drag because the contact area is very small (only one cell). In contrast when a micro-knife cuts tissue having many cells, designing the knife to be as thin as possible minimizes the resulting drag force exerted upon the knife. Accordingly, unlike conventional thicker knives a thin micro-knife does not push tissue very far in a lateral direction. Also, the depth of the initial cut caused by a micro-knife is not very deep. The depth of cut is typically, but not limited to applications where cutting is shallow (e.g., less than 1 mm). Exceeding a depth of cut more than about 20 times the width of the blade of the micro-knife may increase the risk of breaking the blade. Naturally, micro-knife blades shall be optimized for different applications. For example, for cutting 20 microns deep, a 1 micron wide blade may suffice. For cutting 1,000 microns deep, a 50 micron wide blade may be preferred.

For cutting single cells on the bottom of a petri dish, the width of the base of a blade can be several hundred microns wide to allow visual transparency with a microscope. This feature permits alignment of the cutting edge with the target cell. In such a case, drag force doesn't play a role since the depth of cut is exactly one cell regardless of the width of the blade.

These cutting instruments are useful in the area of microsurgery, including surgery performed on single cells. The surface is smooth on the atomic scale, and the cutting edge is sharp on the atomic scale (e.g., radius of curvature less than 500 angstroms, with some variations of the invention ranging between 200 angstroms and 5 angstroms.)

When combined with a rigid filler material, variations of inventive micro-machined blades may be fabricated to have a knife surface or shell (or body shell, blade surface, cutting surface etc.) with the filler material partially or totally reinforcing the knife surface. As used herein, the knife surface, blade surface, or cutting surface refers to the exterior of a shell or similar structure that may be supported with a filler material. Typically, the structure is a shell, but other configurations may be included. For example, the shell may have openings placed therein where such openings do not interfere with the cutting edge formed by the shell.

This reinforced shell configuration permits fabrication of micro-knives having radii of curvature between 5-50 angstroms. As noted above, such radii are significantly less than conventional micro-blades. However, as noted above, variations of the invention include knives with radii of curvature up to 500 angstrom. The reinforcement provided by the rigid filler material prevents the blade surface from deflecting and/ or bending that would otherwise crack the blade surface. In most variations of the device, the smoothness of the blade allows the blade to actually contact the object to be cut. There are no gaps or aberrations in roughness where a cell may be missed by the cutting edge. The small radius of curvature of the cutting edge allows for a small cutting force. It follows that cutting of cells occurs without tearing or otherwise damaging the cells. It is also noted that knives fabricated by the disclosed process will have a cutting edge (or outer shell cutting edge) having a radius of curvature that is less than or equal to a radius of curvature of an adjacent edge of the body portion. This construction is possible mainly due to the fact that the cutting edge or outer edge is deposited first. Then the body portion is deposited within the cutting edge.

BRIEF DESCRIPTION OF THE DRAWINGS

FIGS. 19A-20 illustrate examples of a knife blade according to the present invention.

DETAILED DESCRIPTION OF THE INVENTION

FIGS. 1 to 18 and the accompanying text illustrate one possible method of manufacturing a micro machined device according to a variation of the present invention. It will be appreciated that variations of the following example are within the scope of the invention.

Figure 1:
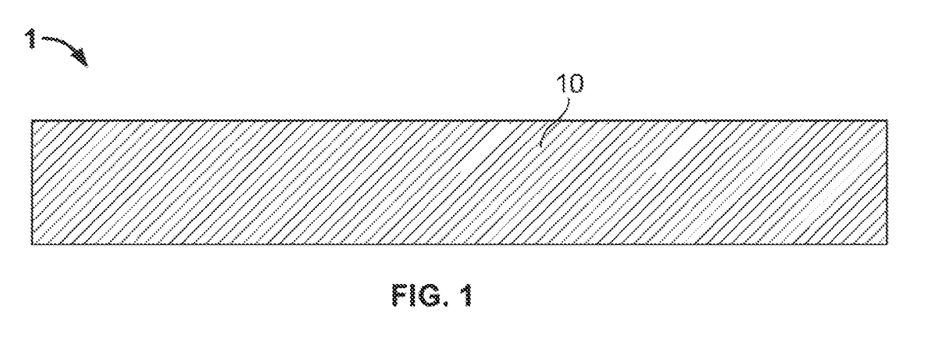
FIG. 1 illustrates a basic wafer assembly.

FIG. 1 shows the start of a wafer assembly 1 as being a cross section of a (100) single crystal silicon wafer 10 that will be used to form the mold for the knife.

Figure 2:
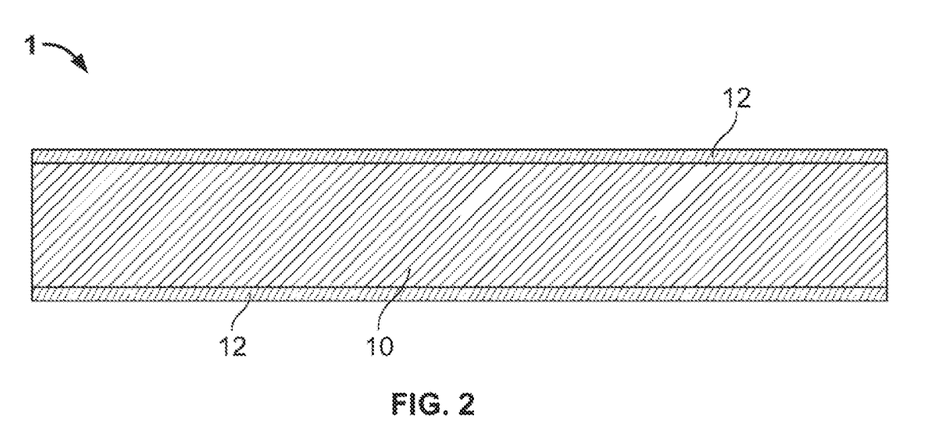
FIG. 2 illustrates the wafer assembly after a layer of silicon dioxide is applied.

FIG. 2 shows a cross section of the wafer assembly 1 comprising the (100) single crystal silicon wafer with a layer of silicon dioxide 12 grown on it. Typically the silicon dioxide layer 12 is about 1 micron thick, and is grown at 1100 degrees C. in oxygen with steam present.

Figure 3:
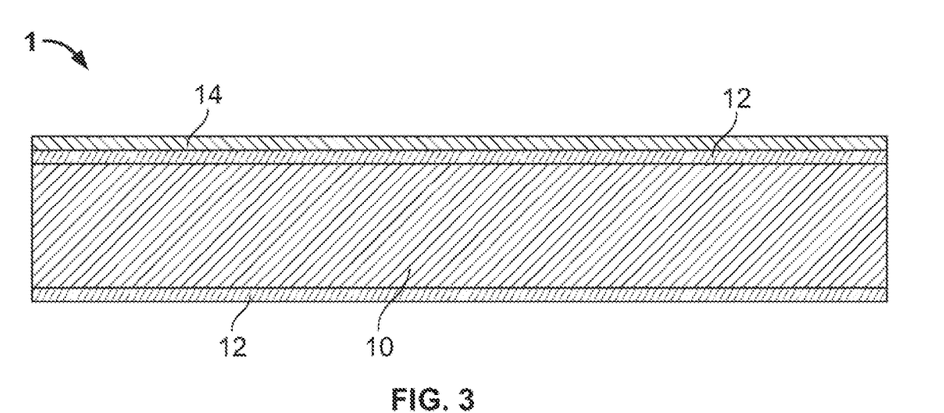
FIGS. 3 and 4 illustrate placement of a photoresist layer and patterning the photoresist layer respectively.

FIG. 3 shows the addition of a layer of photoresist 14 applied over the silicon dioxide layer 12. The photoresist 14 may be applied in a number of ways (e.g., spin applied over the oxide layer.)

Figure 4:
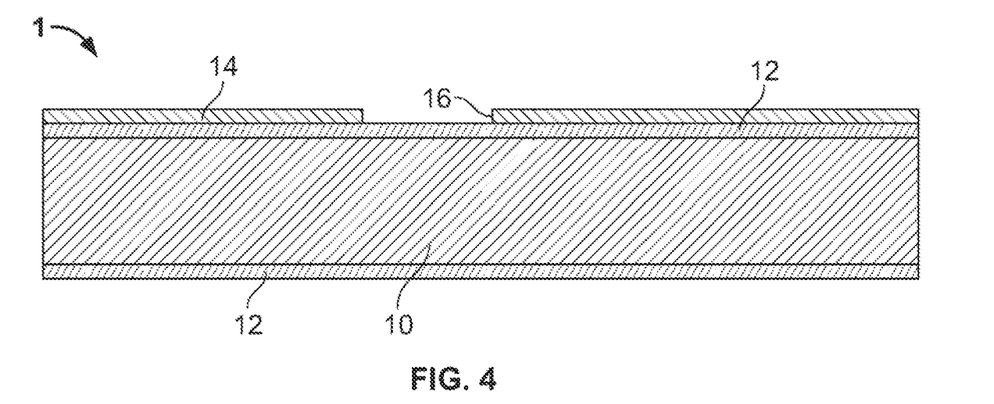

FIG. 4 illustrates the photoresist once patterned to reveal exposed areas 16 for etching. Typically, the exposed areas 16 are rectangular in shape to allow for the length of the blade. Although the figure illustrates a single area being exposed, the procedure can include exposing multiple areas on the assembly 1.

Figure 5:
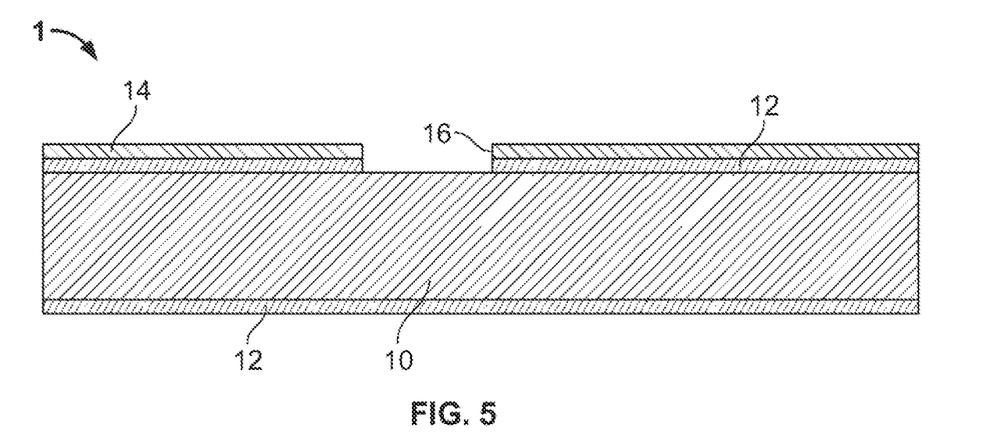
FIG. 5 illustrates etching through the patterned photoresist layer to pattern the silicon dioxide layer.

FIG. 5 shows the assembly after etching away of the silicon dioxide layer 12 that was previously exposed during patterning of the photoresist. This step exposes the single crystal silicon 10. Typically, etching of the silicon dioxide layer 12 occurs by using aqueous hydrofluoric acid/ammonium fluoride solution) to expose the underlying silicon.

Figure 6:
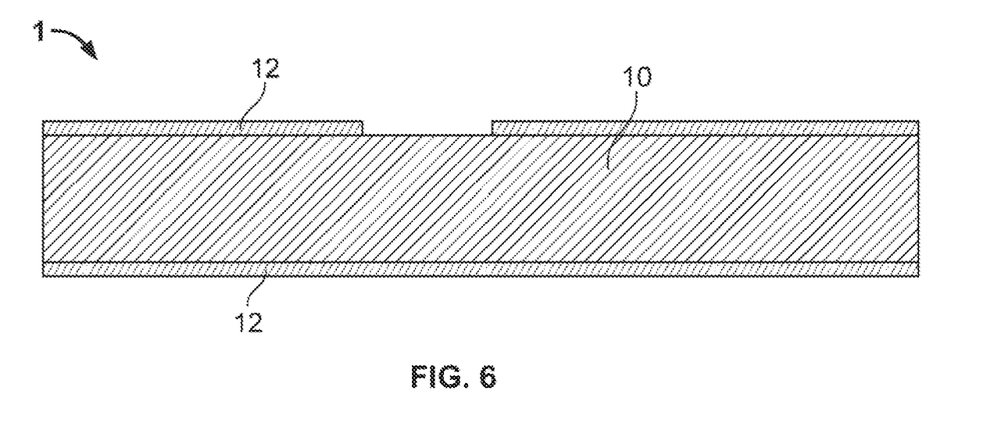
FIGS. 6 and 7 illustrate removal of the photoresist layer and etching a knife channel into the wafer assembly respectively.

As shown in FIG. 6, the photoresist is removed leaving the pattern in the silicon dioxide layer 12 on the single crystal silicon 10.

Figure 7:
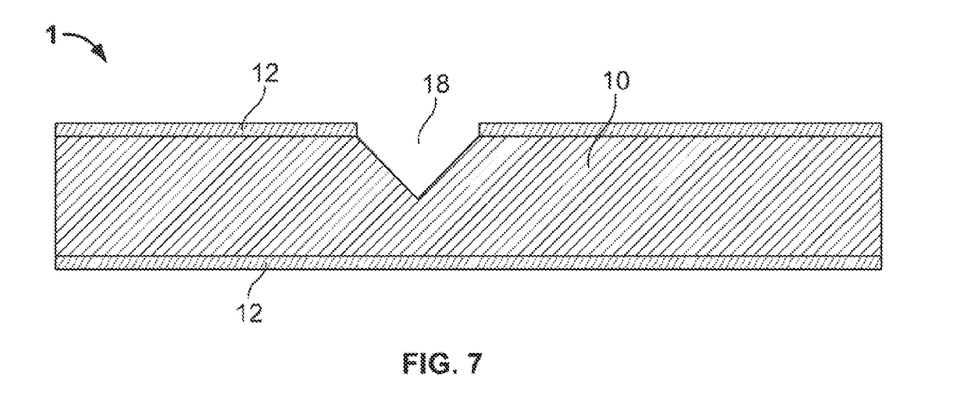

FIG. 7 illustrates the assembly after etching of the knife mold pits 18. In one example, the knife mold pits 18 may be etched in the single crystal silicon 10 by using aqueous potassium hydroxide (e.g., using 40 wt % KOH in water, at 60 degrees C.).

Figure 8:
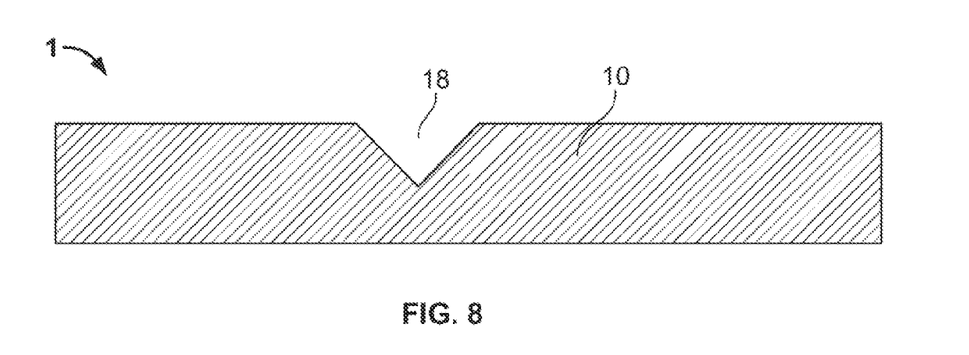
FIG. 8 illustrates removal of the oxide layer.

Once the knife mold pits 18 are etched, the remaining oxide layer is removed (e.g., using concentrated HF). This process leaves a pattern of an elongate channel 18 within the substrates or wafer 10 material.

Figure 9:
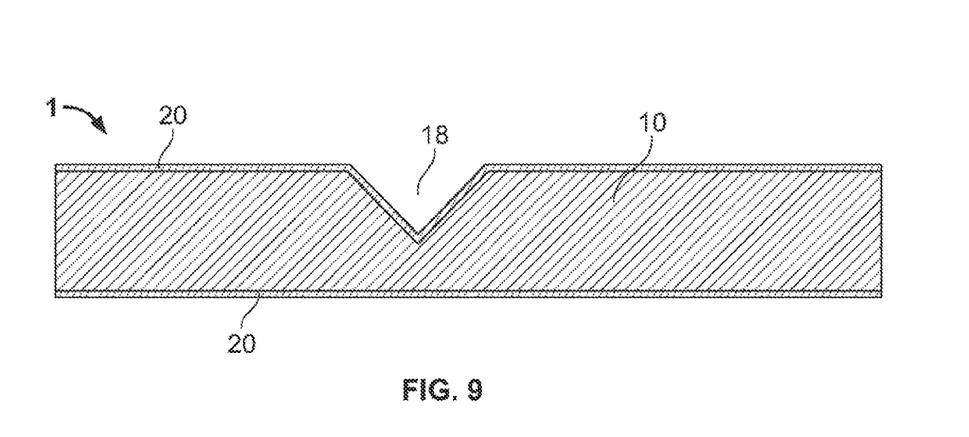
FIG. 9 illustrates an optional step of placing a sharpening layer on the wafer assembly.

FIG. 9 shows the performance of an optional "oxidation sharpening" step allowing for improved control in the overall manufactured knife. In such a step, about 0.1 micron of a sharpening layer 20, (e.g., silicon dioxide) is grown in dry oxygen at a temperature that may range from about 900 to about 950 degrees C. This process allows fine control of the sidewall slope at the cutting edge.

Figure 10A:
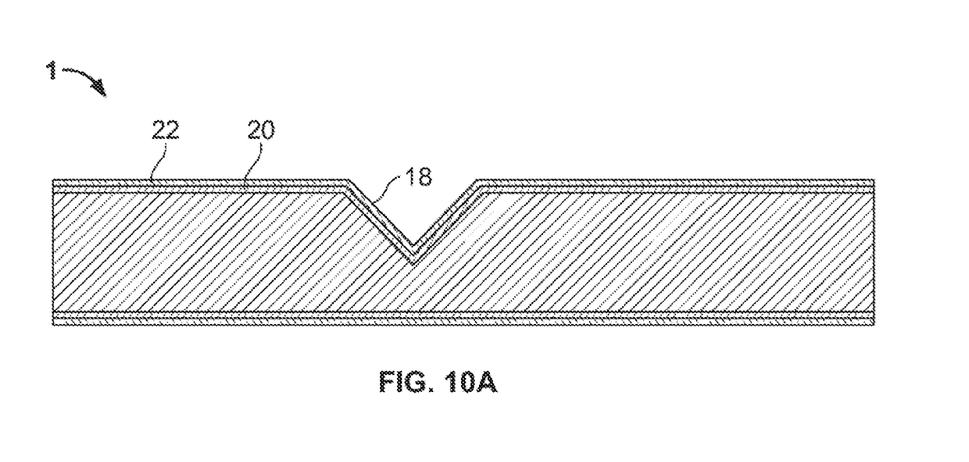
FIG. 10A illustrates placing an exterior knife surface into the etched wafer.

FIG. 10A illustrates the formation of an exterior knife surface on the wafer assembly 1. In this example a film of silicon nitride 22 is deposited on the wafer assembly 1. As noted herein, other materials can be used in place of silicon nitride. In any case, the deposited film forms a shell structure 22 in the wafer assembly 1. As shown below, the interior knife body will be deposited within the exterior knife shell 22.

Fabrication of the knife in this manner, namely that the interior knife body is deposited within the shell created by the exterior knife surface, allows for smaller sizes when creating the blade edge of the exterior knife shell 22. As the blade edge radius of curvature is always less than a radius of curvature of an edge formed by the filler body 24. In this construction, the filler body reinforces the existing exterior knife shell 22. If the exterior knife shell were deposited on an interior filler body, then the blade edge would be greater than a corresponding edge of the filler material.

Figure 10B:
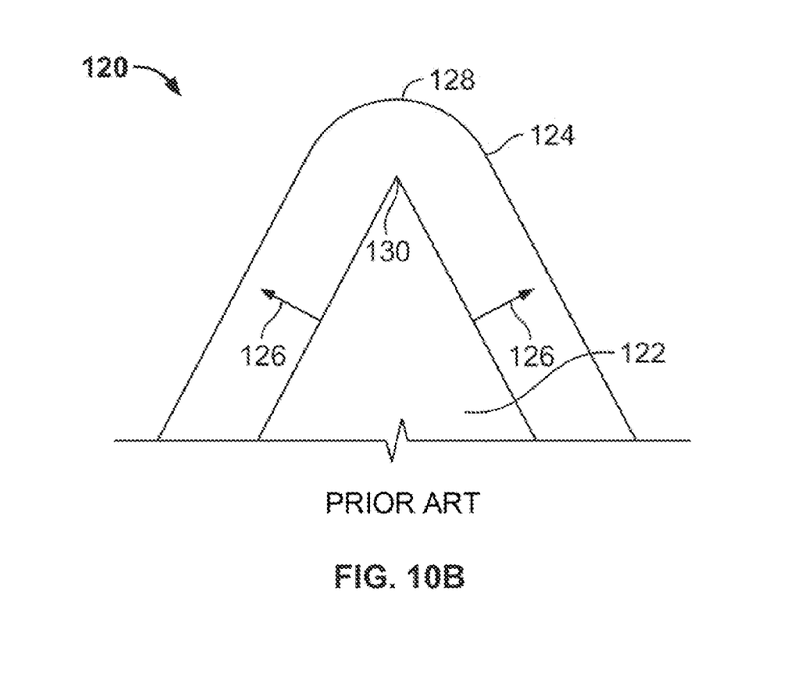
FIGS. 10B-10C illustrate previous devices in comparison to the present devices where a radius of curvature of an exterior shell is less than or equal to a radius of curvature of an interior edge.
Figure 10C:
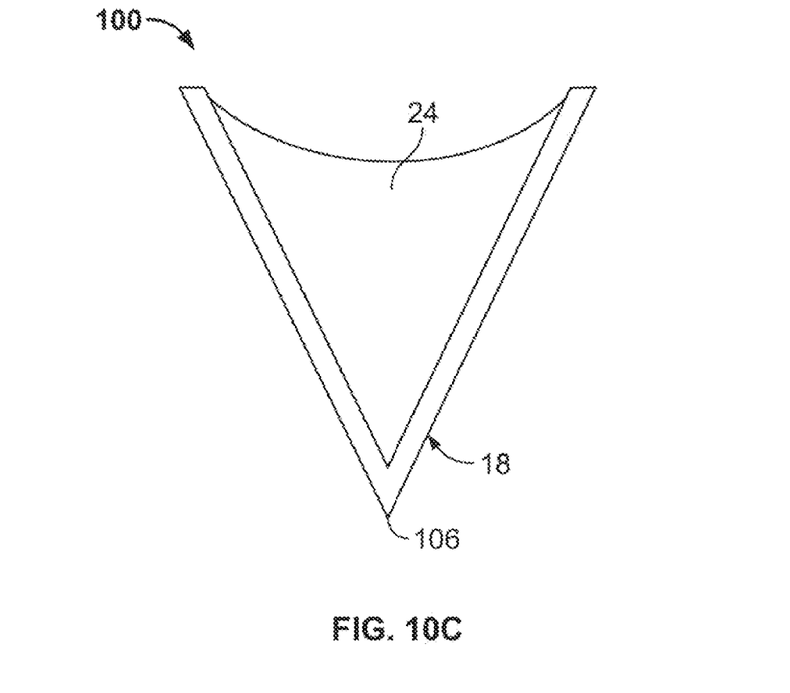

FIGS. 10B to 10C illustrate this distinction. FIG. 10B shows a blade 120 where the interior material 122 is coated with an exterior layer 124, Since the exterior layer 124 is deposited upon the interior material 122, the dimension of the blade grows as shown by arrows 126. Accordingly, the radius of curvature of the exterior edge 128 will always be greater than a corresponding radius of curvature of an interior edge 130 FIG. 10C illustrates a blade 100 fabricated as disclosed herein. In this variation, the blade 100 exterior shell 18 is formed with the body material 24 deposited within the shell 18. Accordingly, since the blade shell 18 is reinforced, a cutting edge 106 formed by the exterior knife shell 18 has an exterior radius of curvature that is less than or equal to the interior radius of curvature.

Variations of the invention include an exterior knife shell 22 layer of about 1 micron thick. However, the invention may also contemplate layers that are less than or greater than 1 micron. In one example, the exterior knife shell 22 may be 0.01 microns thick. Silicon-rich low stress silicon nitride may be deposited by low pressure chemical vapor deposition (LPCVD) using ammonia, and dichlorosilane at 835 degrees C. Various other materials may be used in as the exterior knife shell 22. For example, stoichiometric $Si_3N_4$, silicon carbide, boron carbide, boron nitride, diamond, amorphous carbon, any hard material that can be deposited as a thin film, as well as any combination of materials and any suitable ceramic, metal, mineral, crystalline, or plastic material may be used so long as such materials may form a blade edge as described herein.

Figure 11:
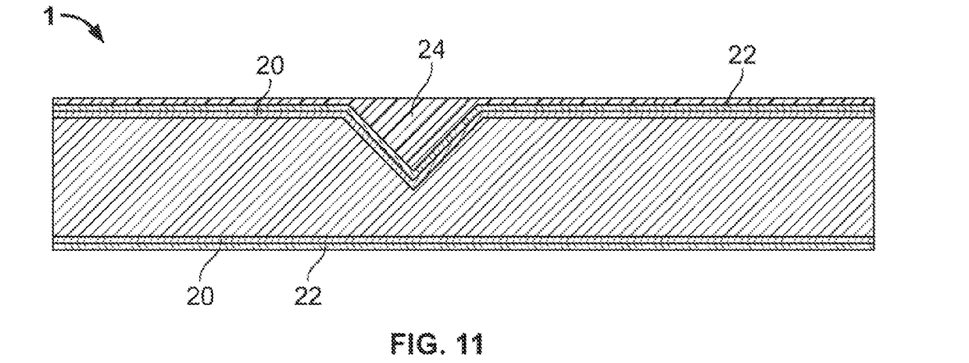
FIGS. 11 and 12 illustrate placement of a body portion into the exterior knife surface and placement of a wafer on the body portion.

FIG. 11 illustrates filling of the mold formed by the exterior knife shell 22 with a body material 24. For example, a slurry of glass frit (for example IP900-vwg from Ferro Corp) is spin applied on the wafer to fill, or partially fill, the exterior knife shell 22 mold cavities, as well as coat the horizontal surface. Then the slurry is dried and fired (typically in oxygen at 950 degrees C. for 10 minutes) to melt the glass particles and form a continuous film of glass which must then be annealed (e.g., 560 degrees C. for 30 minutes).

In an alternative construction, an epoxy fills the exterior knife shell 22 mold so that the epoxy serves as the filler or body portion 24 for the blade.

In any case, the material forming the body portion 24 will be rigid so that it provides sufficient mechanical support for the thinner shell of the exterior knife shell 22.

As noted herein, the filler material may be a glass, epoxy, polycrystalline silicon, ceramic, glass-ceramic, silicon dioxide, or other material. It is noted that placement of the glass frit, (or other filler material) into the shell or exterior knife surface of the blade allows fabrication of a knife where the outer cutting surface or cutting edge will have a radius of curvature that is set by the fabrication process, which allows for a smaller radius of curvature (as compared to a cutting surface that is deposited on a body material). Accordingly, the radius of the outer cutting surface can be as small as the manufacturing process allows. In contrast, when depositing the cutting surface onto an existing body portion, the radius of curvature of the cutting edge will always be greater than the smallest possible radius achievable manufacturing the body portion edge. In some variations of the invention, the hardness of the body portion will be selected to be less than a hardness of the shell/exterior blade portion.

In an alternate variation, the filler or body portion is not required to completely fill the shell of the mold. Instead, the filler/body portion 24 can be a coating of sufficient thickness to provide the mechanical support, required for a given application. Such a coating (e.g., of glass or other material) can start at about 1 micron in thickness. The maximum thickness can be anywhere up to the filling of the mold. As noted above, such coatings may be applied by any of the known methods of depositing material (e.g., sputtering, thermal evaporation, e-beam evaporation, low pressure chemical vapor deposition, etc). For example, in the above case of glass, films of this material can be conveniently deposited by rf sputtering, or by thermal evaporation, usually followed by annealing (typically at about 560 C) to minimize stress.

Figure 12:
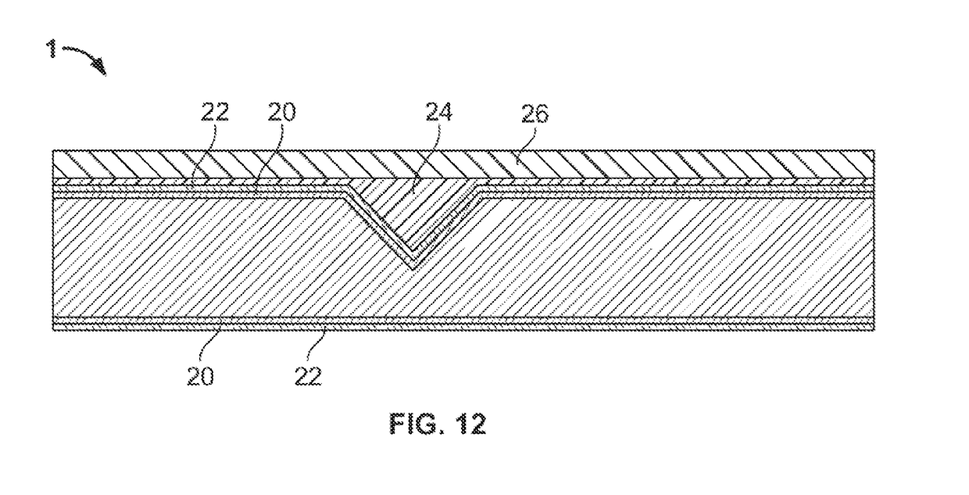

FIG. 12 illustrates optionally bonding a wafer or substrate 26 (e.g., Pyrex, or silicon) bonded on to the wafer assembly 1. If glass was used as the filler body, then the bonding can be done by heating in a furnace to 950 degrees C. for 10 minutes Alternatively the bonding can be done with a film of epoxy between the glass wafer 26 and body filler 24. The Pyrex wafer may be thinned (typically by lapping) to any desired thickness (typically about 100 microns). Alternatively the wafer can be thinned prior to step 11, although it must then be handled carefully to avoid breakage. In any case, the substrate may form a base for the knife blade.

FIGS. 13-18 show an example of processing the wafer assembly 1 to extract a completed (but unshaped) knife blade 100.

Figure 13:
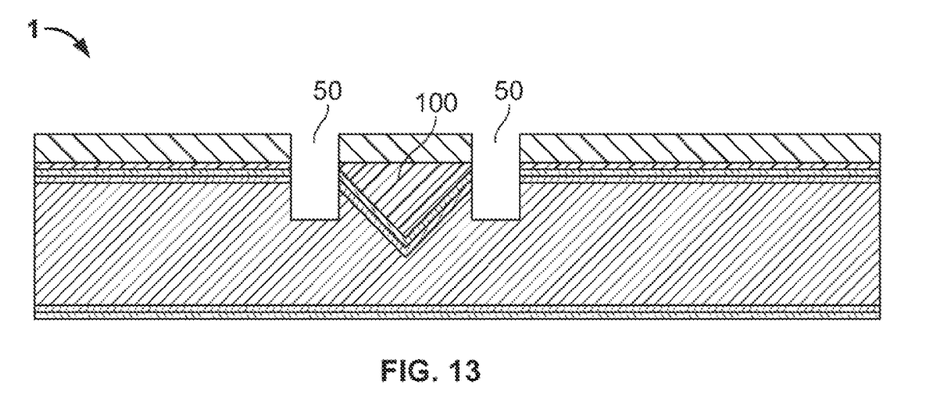
FIGS. 13-18 illustrate processing of the wafer assembly to remove the fabricated knife blade.

FIG. 13 shows a cross sectional view of the assembly 1 after cutting grooves 50 (e.g., by a dicing saw) in the assembly 100. The grooves 50 define the 4 sides (width and length) of the individual knife blades 100.

Figure 14:
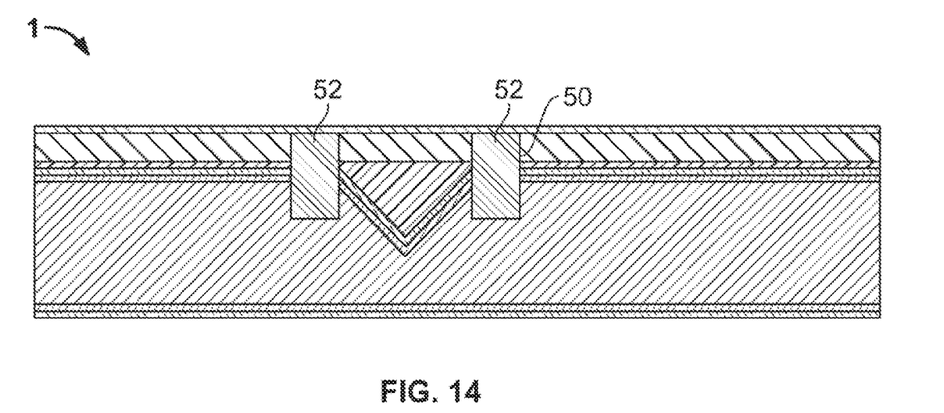

FIG. 14 shows a wax-like material 52 applied to cover the horizontal surface of the wafer 1 and rill the grooves 50. The wax-like material 52 provides protection from the etchant to be used in the next step.

Figure 15:
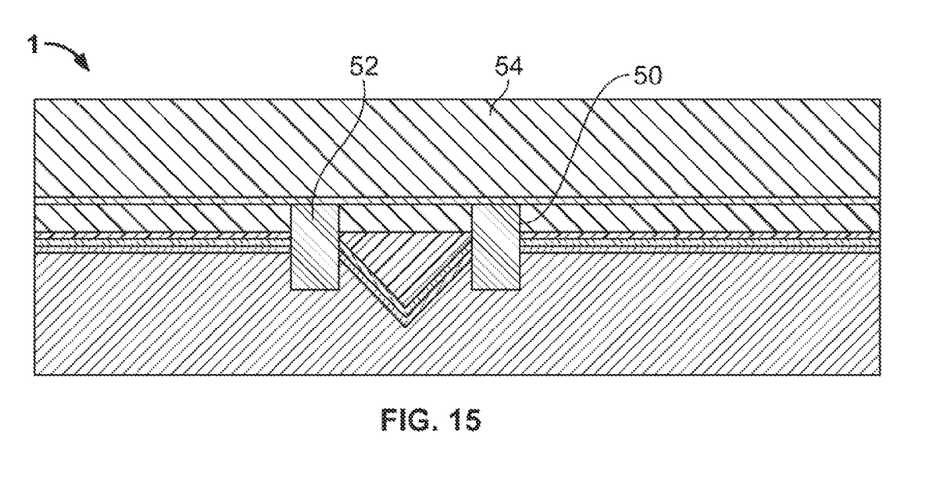

FIG. 15 illustrates softening the wax-like material and applying a handle wafer 54 (e.g., pyrex or oxide coated silicon) onto the wax. Then the oxide and nitride layers are removed from the backside of the mold wafer (e.g., using lapping, grinding, or chemical etching, or plasma etching).

Figure 16:
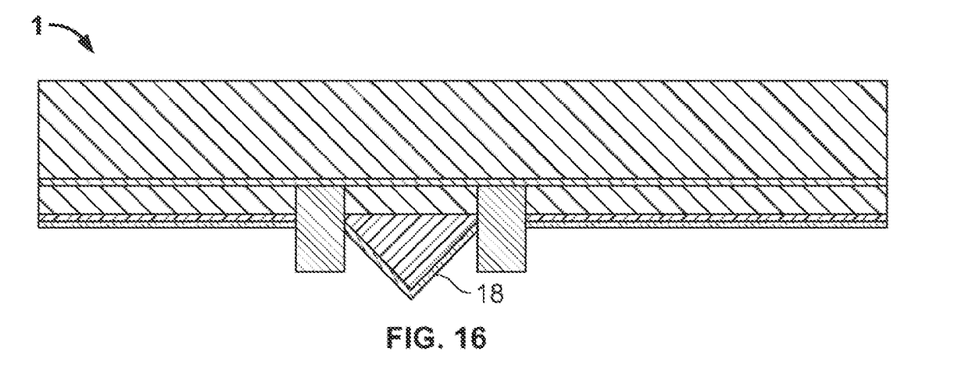

FIG. 16 shows the wafer assembly 1 after removal of the silicon. For example, the wafer can be put into etchant such as aqueous tetramethylammonium hydroxide (e.g., 25 wt % TMAH in water, at 60 degrees C.) to dissolve all of the silicon from the mold of the exterior cutting surface 18 of the wafer assembly 1.

Figure 17:
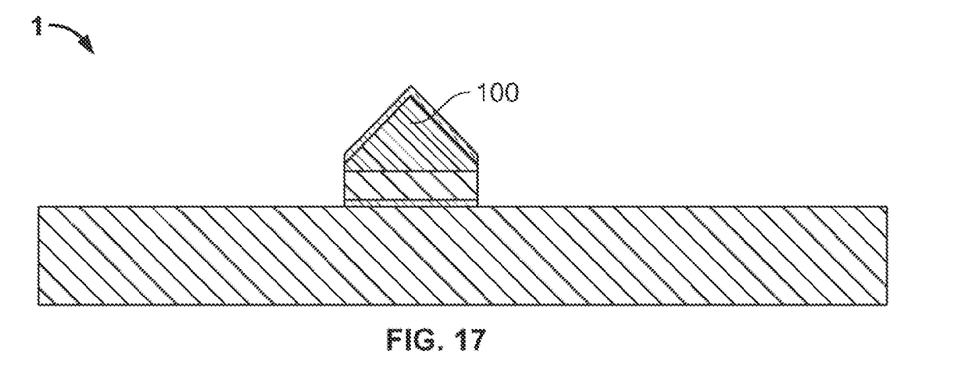
Figure 18:
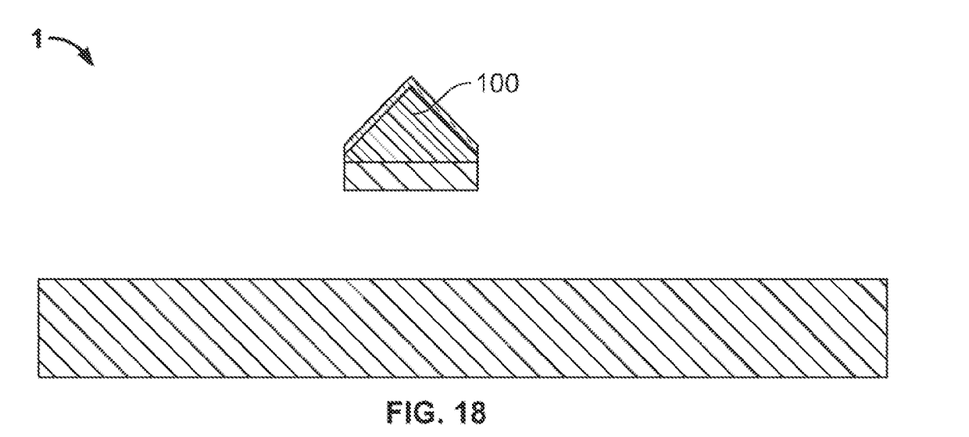

FIG. 17 illustrates the assembly after removal of any excess wax. For example, the excess wax can simply be heated up and melted enough that the individual knife blades 100 can be removed (as shown in FIG. 18).

Figure 19A:
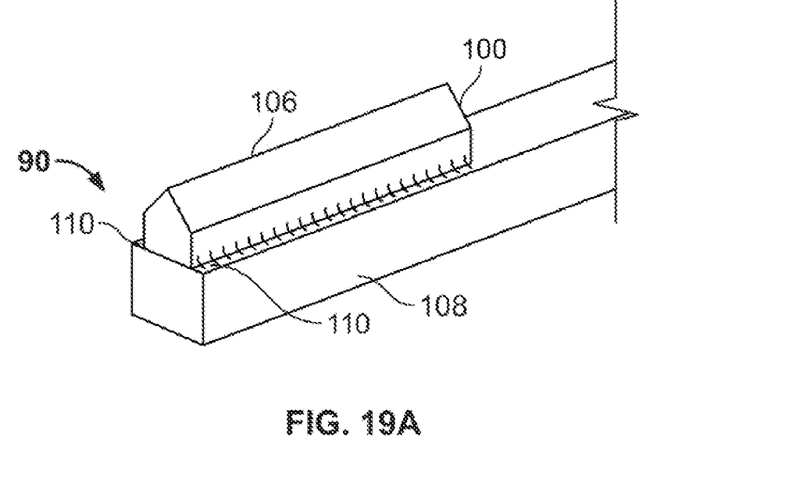

FIG. 19A shows a perspective view of a knife 90 according to the present invention. As shown, a knife blade 100 is cleaned, and bonded to a supporting handle 108 (e.g., by reflowing glass frit, or by epoxy 110).

Figure 19B:
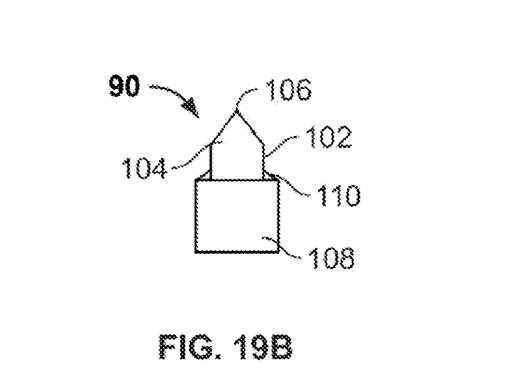

FIG. 19B shows an end view of the knife 90, the micro-machined knife may have a cross sectional area of a substantially pentagonal shape. However, other shapes are also possible. For example, the cross sectional shape may be trapezoidal, triangular, etc.

As shown in FIG. 19B, the micro-machined knife 90 includes a blade 100 having a cutting surface 102 or shell located over body portion 104. In variations of the invention, the cutting surface 102 comprises a hard material as described herein. In additional variations, the body portion 104 comprises a rigid material that provides sufficient support to the cutting surface to prevent deflection of the cutting surface. As a result, the exterior thin cutting surface 102 on a knife may be less prone to cracking or damage because of the rigid body portion. As noted above, the cutting surface may comprise silicon nitride.

The blade edge 106 of the knife 100 is formed at the intersection of the two adjacent surfaces and may have a radius of curvature no greater than 500 angstroms. As noted herein, because the blade edge 106 is formed prior to the body portion 104, the radius of the blade edge 106 may be the smallest attainable radius given the processing limitations.

As noted above, the shell of the exterior cutting surface 102 may be formed within the etched channel of the substrate. After formation, the body portion may be applied as a filler (e.g., epoxy or glass) within the cavity or channel. Variations of the invention include a body portion that is partially filled with the epoxy or glass. Alternatively, or in combination, a third material may be used behind the epoxy/glass to completely fill the shell 102.

The knife blade 100 may be designed to be clear or transparent to allow visibility through the knife body. As such, the substrate or base 108 may be constructed from a transparent material as well. In the example provided above, the substrate comprises a glass wafer. In some variations, the materials are transparent or deposited in a sufficiently thin layer that they are functionally transparent. Moreover, the handle 108 may also be transparent.

Figure 20:
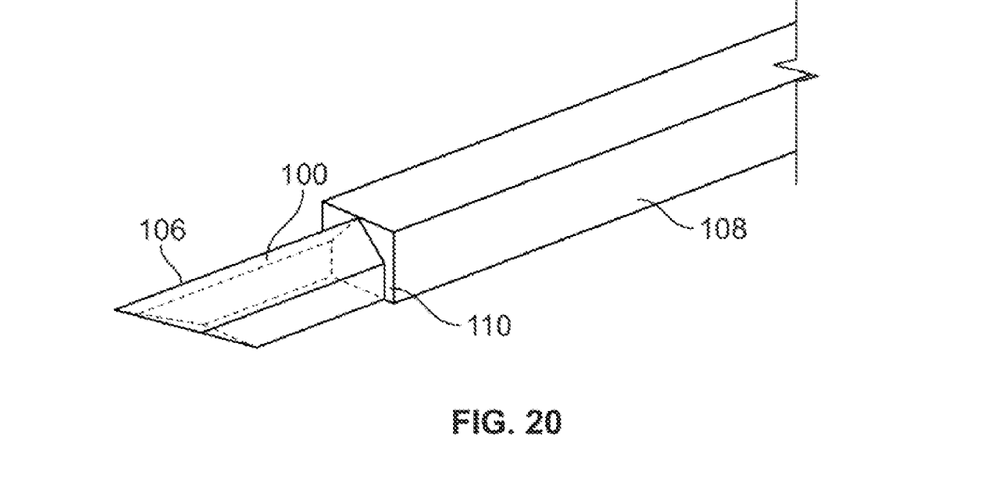

FIG. 20 illustrates an example of the knife body having an end that is sharpened. The opposite end is attached to a handle. The lapping required to produce the illustrated geometry can be performed prior to dissolving the silicon. Shaping the knife body with the silicon in place provides mechanical support to the knife body.

In the configuration shown, the shell obtains mechanical support from the body filler material rather than the handle or any frame. Accordingly, in variations of the device, there is no need for a silicon frame as may be found with other conventional devices. This permits complete removal of the surrounding silicon during the fabrication process. The removal of any frame structure makes it easier to process the blade into various other geometries (e.g., as shown in FIG. 20 where the handle 108 is affixed to the end of the blade 100 while the opposite end is sharpened to a point).

In certain cases, a body filling (or lining) material can be initially applied as a liquid (e.g., epoxy), or can become liquid during processing (e.g., melting glass). In such a case, the liquid material must wet the inside surface of the knife shell (where "wet" means that the liquid is attracted to the surface and spreads out on it). Not wetting means that the liquid does not spread out to cover the surface but typically beads up. For example: molten pyrex glass does not wet lpcvd silicon rich silicon nitride. In such cases, it may be necessary to apply a surface treatment to assist in the wetting process given the chosen body filling material. One example of a surface treatment that improves wetting by molten glass is the application of a thin film of alumina. A convenient way to apply the alumina is to evaporate or sputter aluminum (typically 100 to 1000 angstroms thick), and then heat it in oxygen (air is sufficient) to a temperature sufficient to completely oxidize the aluminum (e.g., 500 C). Wetability is determined by the chemical composition and the microscale roughness of the surface. Typically, a smooth surface is harder to wet while a rough surface is easier to wet. Note that all of the materials in this example (silicon nitride, alumina, and glass) are transparent. Accordingly, for those applications described above, where transparency is desired, the wetting agent shall be transparent as well.

I claim:

1. A micro-machined knife comprising;
   an interior body portion comprising a body material, the body portion having at least a first and second sides which converge in a first direction to intersect forming an interior edge having an interior radius of curvature;
   an exterior knife shell located exterior to at least the first and second sides of the interior body portion, the exterior knife shell comprising a shell material; and
   a cutting edge formed by the exterior knife shell oriented in the first direction and exterior to the interior edge, the cutting edge having an exterior radius of curvature, where the exterior radius of curvature is less than or equal to the interior radius of curvature and the exterior radius of curvature is no greater than 500 angstroms.

2. The micro-machined knife of claim 1, wherein the exterior radius of curvature is no greater than 100 angstroms.

3. The micro-machined knife of claim 2, wherein the exterior radius of curvature is no greater than 50 angstroms.

4. The micro-machined knife of claim 3, wherein the exterior radius of curvature is no greater than 25 angstroms.

5. The micro-machined knife of claim 4, wherein the exterior radius of curvature is between 5 and 25 angstroms.

6. The micro-machined knife of claim 1, further comprising a substrate located on a portion of the interior body portion.

7. The micro-machined knife of claim 6, where the substrate is substantially transparent.

8. The micro-machined knife of claim 1, where the body material comprises a material selected from the group consisting of an epoxy and a glass.

9. The micro-machined knife of claim 1, where the shell material comprises a material selected from the group consisting of silicon nitride, silicon rich silicon nitride, silicon carbide, diamond, boron carbide, boron nitride.

10. The micro-machined knife of claim 1, further comprising a base substrate attached to a portion of the body portion located opposite to the interior edge.

11. The micro-machined knife of claim 1, where the exterior knife shell is approximately 1 micron thick.

12. The micro-machined knife of claim 1, further comprising a handle attached to a portion of the interior body.

13. The micro-machined knife of claim 1, where a first end of the interior body forms a point.

14. The micro-machined knife of claim 1, where a cross sectional area of the interior body portion and exterior knife shell comprises a substantially pentagonal shape.

15. The micro-machined knife of claim 1, where the body material is substantially transparent.

16. The micro-machined knife of claim 1, where the shell material is substantially transparent.

17. A micro-machined knife blade comprising:
    an exterior body having at least two sides which converge in a first direction and form a cavity or channel between the two sides;
    a cutting edge formed by an intersection of the two sides at an exterior of the sides and extending along a length of the cavity or channel, where a radius of curvature of the cutting edge is no greater than 500 angstroms;
    where the exterior body comprises an exterior body material; a body filler located in the cavity or channel between the two sides; and the body filler comprises a body edge adjacent to the cutting edge, where the radius of curvature of the cutting edge is less than or equal to a radius of curvature of the body edge.

18. The micro-machined knife of claim 17, wherein the radius of curvature of the cutting edge is no greater than 100 angstroms.

19. The micro-machined knife of claim 17, wherein the radius of curvature of the cutting edge is no greater than 50 angstroms.

20. The micro-machined knife of claim 17, wherein the radius of curvature of the cutting edge is no greater than 25 angstroms.

21. The micro-machined knife blade of claim 17, where the exterior body is open on each end.

22. The micro-machined knife blade of claim 17, where the body filler substantially fills the cavity or channel of the exterior body.

23. The micro-machined knife blade of claim 17, where the body filler partially fills the cavity or channel of the exterior body.

24. The micro-machined knife blade of claim 23, further comprising an additional material which substantially fills a remaining portion of the cavity or channel of the exterior body.

25. The micro-machined knife blade of claim 17, further comprising a substrate located on a side of the exterior body opposite to the cutting edge.

26. The micro-machined knife blade of claim 17, further comprising a substrate bonded to the body filler on a side of the micro-machined knife blade opposite to the cutting edge.

27. The micro-machined knife blade of claim 17, where the exterior body-material is substantially transparent.

28. The micro-machined knife blade of claim 17, where the body filler is substantially transparent.

29. The micro-machined knife blade of claim 17, where the body filler comprises a material selected from the group consisting of a glass, epoxy, polycrystalline silicon, ceramic, glass-ceramic, and silicon dioxide.

30. The micro-machined knife blade of claim 17, where the exterior body material comprises a material selected from the group consisting of silicon nitride, silicon rich silicon nitride, silicon carbide, diamond, boron carbide, boron nitride.

31. The micro-machined knife blade of claim 17, where the exterior body is approximately 1 micron thick.

32. The micro-machined knife blade of claim 17, where a first end of exterior body forms a point.

33. The micro-machined knife of claim 17, where a cross sectional area of the cavity or channel and exterior body comprises a substantially pentagonal shape.

* * * * *